(12) United States Patent
Heckmeier et al.

(10) Patent No.: US 6,696,111 B2
(45) Date of Patent: Feb. 24, 2004

(54) LIQUID-CRYSTALLINE MEDIUM

(75) Inventors: Michael Heckmeier, Bensheim (DE); Matthias Bremer, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 12 days.

(21) Appl. No.: 09/973,720

(22) Filed: Oct. 11, 2001

(65) Prior Publication Data

US 2003/0001137 A1 Jan. 2, 2003

(30) Foreign Application Priority Data

Oct. 12, 2000 (DE) .......................... 100 50 405

(51) Int. Cl.⁷ .................. C09K 19/30; C09K 19/20; C09K 19/34; C09K 19/12; C07C 25/24
(52) U.S. Cl. ............... 428/1.1; 252/299.63; 252/299.61; 252/299.67; 252/299.66; 570/128
(58) Field of Search ............ 428/1.1; 252/299.63, 252/299.61, 299.67; 570/127, 128, 129

(56) References Cited

U.S. PATENT DOCUMENTS

| | | | | |
|---|---|---|---|---|
| 5,487,845 A | * | 1/1996 | Reiffenrath et al. | 252/299.63 |
| 5,536,442 A | * | 7/1996 | Reiffenrath et al. | 252/299.01 |
| 5,641,429 A | * | 6/1997 | Reiffenrath et al. | 252/299.61 |
| 5,948,318 A | * | 9/1999 | Miyazawa et al. | 252/299.63 |
| 6,013,198 A | * | 1/2000 | Miyazawa et al. | 252/299.63 |
| 6,117,360 A | * | 9/2000 | Miyazawa et al. | 252/299.63 |

FOREIGN PATENT DOCUMENTS

| | | |
|---|---|---|
| DE | 3022818 A1 | 1/1982 |
| EP | 0334911 B1 | 10/1989 |
| EP | 0441932 B1 | 8/1991 |
| EP | 0761799 A1 | 3/1997 |
| JP | 08-143498 * | 6/1996 |

OTHER PUBLICATIONS

English translation for JP 08–143498 by computer, http://www6.ipdl.jpo.go.jp/Tokujitu/PAJdetail.ipdl?N0000=60&N0120=01&N2001=2&N3001=H08–143498.*

* cited by examiner

Primary Examiner—Shean C. Wu
(74) Attorney, Agent, or Firm—Millen, White, Zelano, Branigan, P.C.

(57) ABSTRACT

A liquid-crystalline medium based on a mixture of polar compounds of positive dielectric anisotropy, characterized in that it comprises one or more compounds of the general formula IA and/or IB

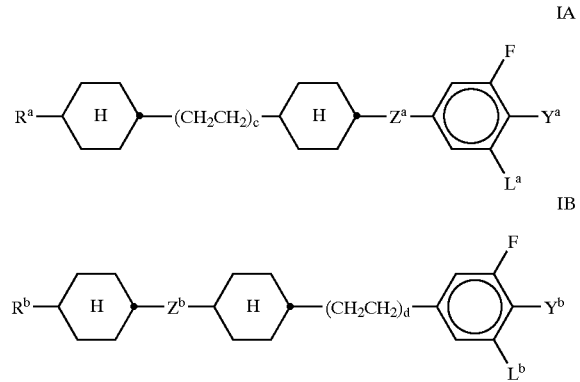

in which $R^a$, $R^b$, $Y^a$, $Y^b$, $Z^a$, $Z^b$, $L^a$, $L^b$, c and d are as defined herein, is suitable for use in MLC, TN and STN displays.

29 Claims, No Drawings

LIQUID-CRYSTALLINE MEDIUM

The present invention relates to a liquid-crystalline medium, and to the use thereof for electro-optical purposes, and to displays containing this medium.

Liquid-crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapor pressure are desired.

Matrix liquid-crystal displays of this type are known. Non-linear elements which can be used for individual switching of the individual pixels are, for example, active elements (i.e. transistors). The term "active matrix" is then used, where a distinction can be made between two types:
1. MOS (metal oxide semiconductor) or other diodes on a silicon wafer as substrate.
2. Thin-film transistors (TFTs) on a glass plate as substrate.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. The latter technology is being worked on intensively worldwide.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully color-capable displays, in which a mosaic of red, green and blue filters is generally arranged in such a way that a filter element is opposite each switchable pixel.

The TFT displays usually operate as TN cells with crossed polarizers in transmission and are illuminated from the back.

The term MLC displays here covers any matrix display with integrated non-linear elements, i.e., besides the active matrix, also displays with passive elements, such as varistors or diodes (MIM=metal-insulator-metal).

MLC displays of this type are particularly suitable for TV applications (for example pocket TVs) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not meet today's requirements.

Besides liquid-crystal displays which use back lighting, i.e. are operated transmissively and optionally transflectively, there is also particular interest in reflective liquid-crystal displays. These reflective liquid-crystal displays use the ambient light for information display. They thus consume significantly less energy than back-lit liquid-crystal displays of corresponding size and resolution. Since the TN effect is characterised by very good contrast, reflective displays of this type are readily legible even under bright ambient conditions. This is already known of simple reflective TN displays, as used, for example, in wristwatches and pocket calculators. However, the principle can also be applied to high-quality, higher-resolution active matrix-addressed displays, such as, for example, TFT displays. Here, as is already the case in the generally conventional transmissive TFT-TN displays, the use of liquid crystals of low birefringence ($\Delta n$) is necessary in order to achieve low optical retardation (d·$\Delta n$). This low optical retardation results in a low viewing-angle dependence of the contrast, which is usually acceptable (cf. DE 30 22 818). In reflective displays, the use of liquid crystals of low birefringence is much more important than in transmissive displays, since in reflective displays, the effective layer thickness through which the light passes is approximately twice as great as in transmissive displays of the same layer thickness.

Advantages of reflective displays over transmissive displays, besides the lower power consumption (no back-lighting necessary), are the space saving, which results in a very low construction depth, and the reduction in problems caused by temperature gradients through different heating-up due to the back-lighting.

SUMMARY OF THE INVENTION

There thus continues to be a great demand for MLC displays having very high specific resistance at the same time as a large working-temperature range, short response times even at low temperatures and low threshold voltage which do not have these disadvantages, or only do so to a reduced extent.

In TN (Schadt-Helfrich) cells, media are desired which facilitate the following advantages in the cells:

broadened nematic phase range (in particular down to low temperatures)

switchability at extremely low temperatures (outdoor use, automobiles, avionics)

increased stability to UV radiation (longer life)

lower threshold (addressing) voltage, and low birefringence for an improved viewing angle range.

The media available from the prior art do not enable these advantages to be achieved while simultaneously retaining the other parameters.

In supertwisted cells (STN), media are desired which enable greater multi-plexability and/or lower threshold voltages and/or broader nematic phase ranges (in particular at low temperatures). To this end, a further extension of the available parameter latitude (clearing point, smectic-nematic transition or melting point, viscosity, dielectric parameters, elastic parameters) is urgently desired.

An object of the invention is to provide media for MLC, TN or STN displays of this type, in particular for reflective MLC displays, which do not have the above-mentioned disadvantages, or only do so to a lesser extent, and preferably at the same time have very high specific resistances and low threshold voltages.

Upon further study of the specification and appended claims, further objects and advantages of this invention will become apparent to those skilled in the art.

It has now been found that these objects can be achieved if media according to the invention are used in displays. The media according to the invention are particularly suitable for low $V_{th}$ applications and are distinguished by their excellent low-temperature behavior.

The invention thus relates to a liquid-crystalline medium based on a mixture of polar compounds of positive dielectric anisotropy, characterized in that it comprises one or more compound(s) of the general formula IA and/or IB

IA

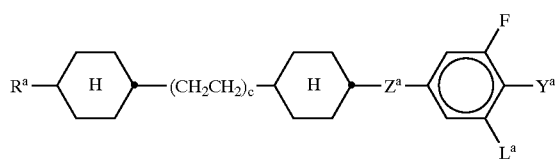

IB

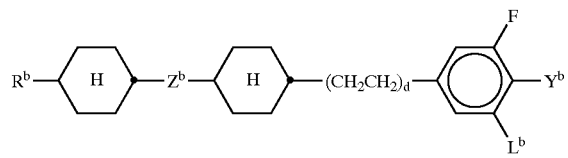

in which $R^a$ and $R^b$ are each, independently of one another, an alkenyl radical having up to 15 carbon atoms which is unsubstituted, mono-substituted by CN or $CF_3$ or at least monosubstituted by halogen, where, in addition, one or more $CH_2$ groups in these radicals may each, independently of one another, be replaced by —O—, —S—,

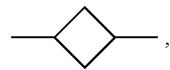

—CO—, —CO—O—, —O—CO— or —O—CO—O— in such a way that O atoms are not linked directly to one another, $Y^a$ and $Y^b$ are each, independently of one another, F, Cl, $SF_5$, NCS, or a halogenated alkyl, alkoxy, alkenyl or alkenyloxy radical having up to 5 carbon atoms, $L^a$ and $L^b$ are each, independently of one another, H or F, $Z^a$ and $Z^b$ are each, independently of one another, —COO—, —$CH_2O$—, —$OCH_2$—, —$C_2F_4$—, —$CF_2O$—, —$OCF_2$— or a single bond, and c and d are each, independently of one another, 1 or 2.

The compounds formulas IA and IB have a broad range of applications. Depending on the choice of substituents, these compounds can serve as base materials of which liquid-crystalline media are predominantly composed; however, it is also possible to add compounds of the formulas IA and/or IB to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula IA or IB are colorless and form liquid-crystalline mesophases in a temperature range which is favorably located for electro-optical use. They are stable chemically, thermally and to light.

Similar compounds containing an alkyl side chain are disclosed in EP 0 761 799 A1.

Compared with the compounds containing an alkyl side chain, the compounds according to the invention are distinguished by a higher clearing point a higher Δn value a lower rotational viscosity ($\gamma_1$).

If $Y^a$ and/or $Y^b$ is a halogenated alkyl, alkoxy, alkenyl or alkenyloxy radical, the halogen substituents are preferably F or Cl, especially F.

In the media according to the invention comprising compounds of the formulae IA and IB, $Y^a$ and $Y^b$ are preferably F, Cl, $OCF_3$, $OCHF_2$, $CF_3$, $CHFCF_3$, $CF_2CHF_2$, $C_2H_4CHF_2$, $CF_2CH_2CF_3$, $CHF_2$, $OCH_2CF_3$, $OCH_2CHF_2$, $OCF_2CHF_2$, $O(CH_2)_3CF_3$, $OCH_2C_2F_5$, $OCH_2CF_2CHF_2$, $OCH_2C_3F_7$, $OCHFCF_3$, $OC_2F_5$, $OCF_2CHFCF_3$, $OCH_2CF_2CHFCF_3$, $OCH=CF_2$, $OCF=CF_2$, $OCF=CFCF_3$, $OCF=CF—C_2F_5$, CH=CHF, CH=CF$_2$, CF=CF$_2$, CF$_2$OCF$_3$, in particular F, OCHFCF$_3$, OCF$_3$, OCHF$_2$, OC$_2$F$_5$, OC$_3$F$_7$, OCH=CF$_2$ and CF$_2$OCF$_3$.

Particular preference is given to compounds of the formulae IA and IB in which Y$^a$ and/or Y$^b$ is F or OCF$_3$. L$^a$ and L$^b$ are preferably F, and Z$^a$ and/or Z$^b$ are preferably a single bond, —CF$_2$O— or —COO—. a and b, independently of one another, are preferably 1.

R$^a$ and/or R$^b$ are an alkenyl radical, which may be straight-chain or branched. It is preferably straight-chain and has from 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, 4- or -5-enyl, hept-1-, -2-, -3-, -4-, -5- or -6-enyl, oct-1-, -2-, -3-, 4-, -5-, -6- or -7-enyl, non-1-, -2-, -3-, -4-, -5-, -6-, -7- or -8-enyl, or dec-1, -2-, -3-, -4-, -5-, -6-, -7-, -8- or -9-enyl.

If R$^a$ and/or R$^b$ are an alkenyl radical in which a CH$_2$ group has been replaced by CO or CO—O or O—CO, this may be straight-chain or branched. It is preferably straight-chain and has from 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryoyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R$^a$ and/or R$^b$ is an alkenyl radical which is monosubstituted by CN or CF$_3$, this radical is preferably straight-chain. The substitution by CN or CF$_3$ is in any desired position.

If R$^a$ and/or R$^b$ is an alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds of the formula IA or IB which contain wing groups R$^a$ or R$^b$ which are suitable for polymerization reactions are suitable for the preparation of liquid-crystalline polymers.

Compounds of the formula IA or IB containing branched wing groups R$^a$ or R$^b$ may occasionally be of importance owing to better solubility in the conventional liquid-crystalline base materials, but in particular as chiral dopants if they are optically active. Smectic compounds of this type are suitable as components of ferroelectric materials.

Compounds of the formula IA or IB having S$_A$ phases are suitable, for example, for thermally addressed displays.

The compounds of the formula IA and IB are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail. Furthermore, the compounds of the formulae IA and IB can be prepared as described in EP 0 334 911 B1 and EP 0 441 932 B1.

The invention also relates to the compounds of the formulae IA and IB. Particular preference is given to compounds of the formulae IA and IB in which Z$^a$ and Z$^b$ are —CF$_2$O—, —OCF$_2$— or —CH$_2$CH$_2$—. Particular preference is given to compounds of the formulae IA and IB in which Z$^a$ and Z$^b$ are a single bond. In the compounds of the formulae IA and IB, Y$^a$ and Y$^b$ are preferably F or OCF$_3$. R$^a$ and R$^b$ are preferably vinyl, 1E-alkenyl or 3E-alkenyl.

The invention also relates to electro-optical displays (in particular STN or MLC displays having two plane-parallel outer plates, which, together with a frame, form a cell, having integrated non-linear elements for switching individual pixels on the outer plates, and a nematic liquid-crystal mixture of positive dielectric anisotropy and high specific resistance which is located in the cell) which contain media of this type, and to the use of these media for electro-optical purposes.

The liquid-crystal mixtures according to the invention enable a significant widening of the available parameter latitude.

The achievable combinations of clearing point, viscosity at low temperature, thermal and UV stability and dielectric anisotropy and threshold voltage are superior to previous materials from the prior art.

The requirement for a high clearing point, a nematic phase at low temperature and at the same time a low threshold voltage has hitherto only been achieved to an inadequate extent. Although liquid-crystal mixtures such as, for example, MLC-6848-000 (Merck KgaA, Darmstadt, FRG), have comparable clearing points and low-temperature stabilities, they have, however, both much higher Δn values of about 0.085 and much higher threshold voltages of about ≧1.7 V.

The liquid-crystal mixtures according to the invention, while retaining the nematic phase down to −20° C. and preferably down to −30° C., particularly preferably down to −40° C., enable clearing points above 60° C., preferably above 65° C., particularly preferably above 70° C., simultaneously birefringence values of ≧0.090, preferably ≧0.095, and a low threshold voltage to be achieved, enabling excellent STN and MLC displays, in particular reflective MLC displays, to be obtained. In particular, the mixtures are characterized by low operating voltages. The TN thresholds are at 1.9 V, preferably below 1.7 V, particularly preferably ≦1.5 V.

It goes without saying that, through a suitable choice of the components of the mixtures according to the invention, it is also possible for higher clearing points (for example above 110°) to be achieved at lower dielectric anisotropy values and thus higher threshold voltages or lower clearing points to be achieved at higher dielectric anisotropy values (for example >12) and thus lower threshold voltages (for example <1.5 V) with retention of the other advantageous properties. At viscosities correspondingly increased only slightly, it is likewise possible to obtain mixtures having a greater Δ∈ and thus lower thresholds. The MLC displays according to the invention preferably operate at the first transmission minimum according to Gooch and Tarry [C. H. Gooch and H. A. Tarry, Electron. Lett. 10, 2–4, 1974; C. H. Gooch and H. A. Tarry, Appl. Phys., Vol. 8, 1575–1584, 1975], where, besides particularly favorable electro-optical properties, such as, for example, high steepness of the characteristic line and low angle dependence of the contrast (German Patent 30 22 818), a lower dielectric anisotropy at the second minimum is sufficient at the same threshold voltage as in an analogous display. This enables significantly higher specific resistances to be achieved at the first minimum using the mixtures according to the invention than in the case of mixtures comprising cyano compounds. Through a suitable choice of the individual components and their proportions by weight, the person skilled in the art is able to set the birefringence necessary for a pre-specified layer thickness of the MLC display using simple routine methods. The requirements of reflective MLC displays have been indicated, for example, in Digest of Technical Papers, SID Symposium 1998.

The rotational viscosity $\gamma_1$ at 20° C. is preferably <180 mPa.s, particularly preferably <150 mpa.s. The nematic phase range is preferably at least 80°, in particular at least 90°. This range preferably extends at least from −20° to +65°. Measurements of the capacity holding ratio, also known as the voltage holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula IA and/or IB have an adequate HR for MFMLC displays.

The media according to the invention preferably comprise a plurality of (preferably two or more) compounds of the formula IA and/or IB.

The individual compounds of the formulae IA, IB and II to XV (described below) and their sub-formulae which can be used in the media according to the invention are either known or can be prepared analogously to the known compounds.

Preferred embodiments are indicated below:

The medium comprises one or more compounds of the formulae

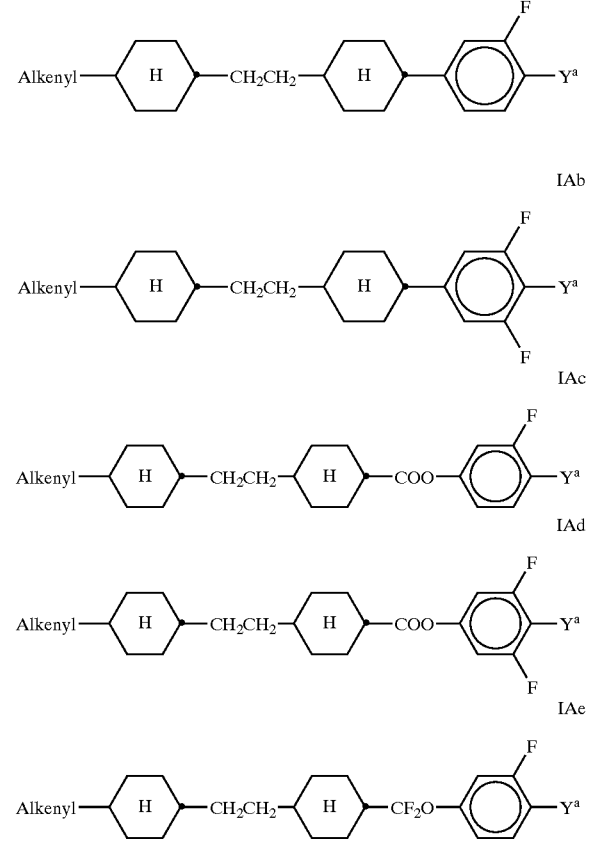

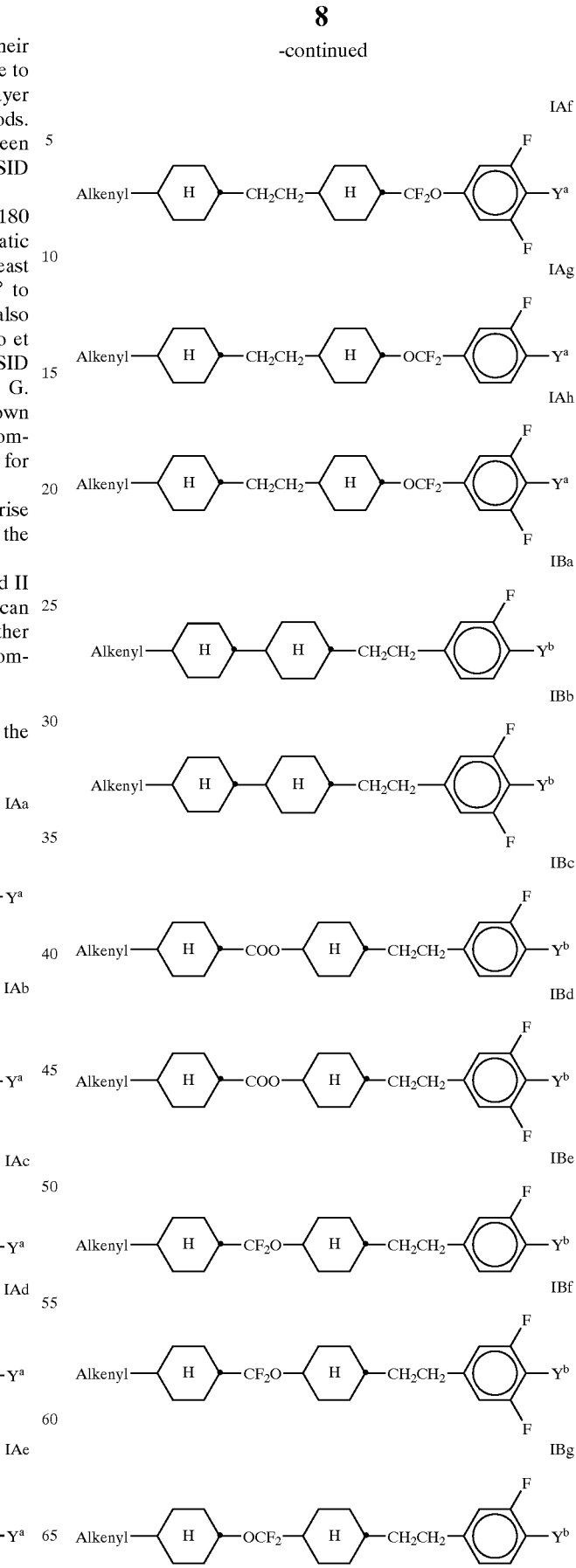

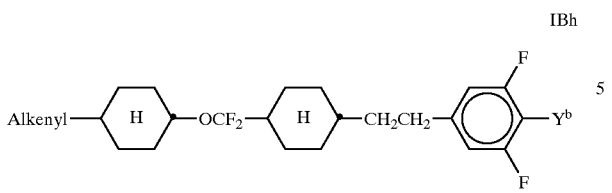

in which

Alkenyl is a 1E- or 3E-alkenyl radical having 2–8 carbon atoms;

Alkenyl is preferably vinyl, $CH_3CH=CH$, $CH_2=CHC_2H_4$ or $CH_3CH=CHC_2H_4$.

The compounds of the formulae IAa–IAh and IBa–IBh are likewise preferred; Alkenyl is preferably vinyl, $CH_3CH=CH$, $CH_2=CHC_2H_4$ or $CH_3CH=CHC_2H_4$.

The medium comprises one or more, preferably one, two or three, compounds of the formula IAa, IAb, IBa and/or IBb;

The medium additionally comprises one or more, preferably three, four or five, compounds selected from the group consisting of the general formulae II to VIII:

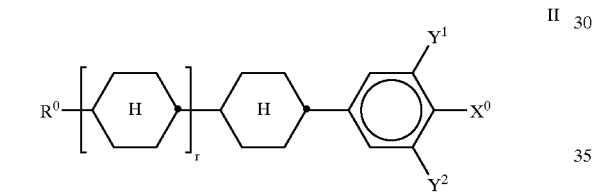

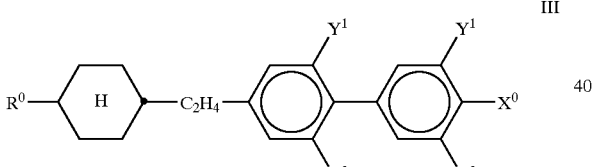

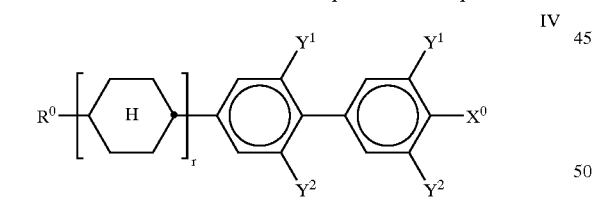

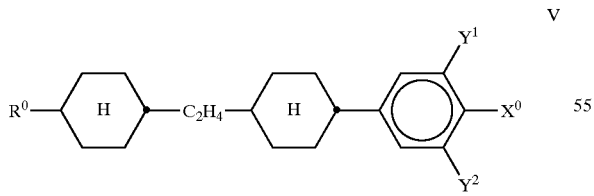

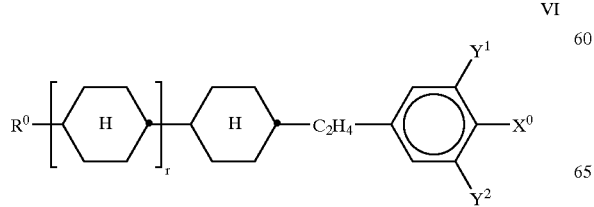

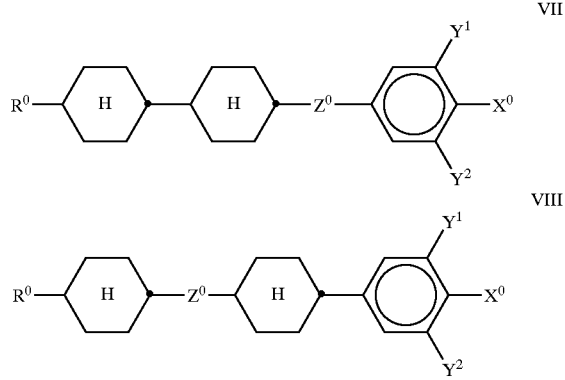

where the compounds of the formulae V and VI (r=1) are not identical with the compounds of the formulae IA and IB.

In the compounds, the individual radicals have the following meanings:

$R^0$: alkyl, oxaalkyl, fluoroalkyl, alkenyloxy or alkenyl, each having up to 9 carbon atoms;

$X^0$: F, Cl, halogenated alkyl or alkoxy having from 1 to 6 carbon atoms, or halogenated alkenyl or alkenyloxy having from 2 to 6 carbon atoms;

$Z^0$: $—C_4H_5—$, $—C_2F_4—$, $—OCH_2—$, $—CH_2O—$, $—CF_2O—$, $—OCF_2—$ or $—CF=CF—$;

$Y^1$ and $Y^2$: each, independently of one another, H or F;

r: 0 or 1.

The medium preferably comprises two, three, four or five compounds of the formula II;

The medium preferably comprises one or more, in particular one or two, alkenyl compounds selected from the group consisting of the compounds

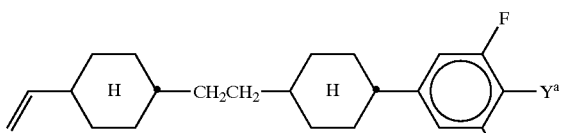

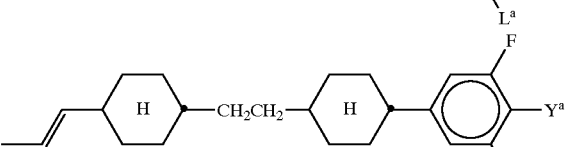

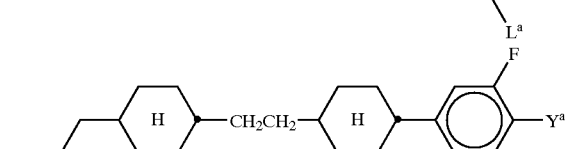

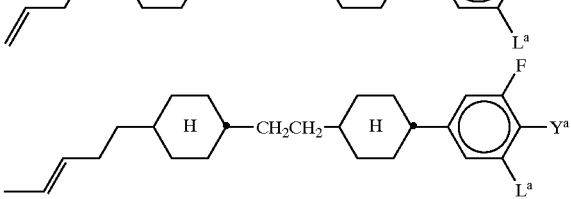

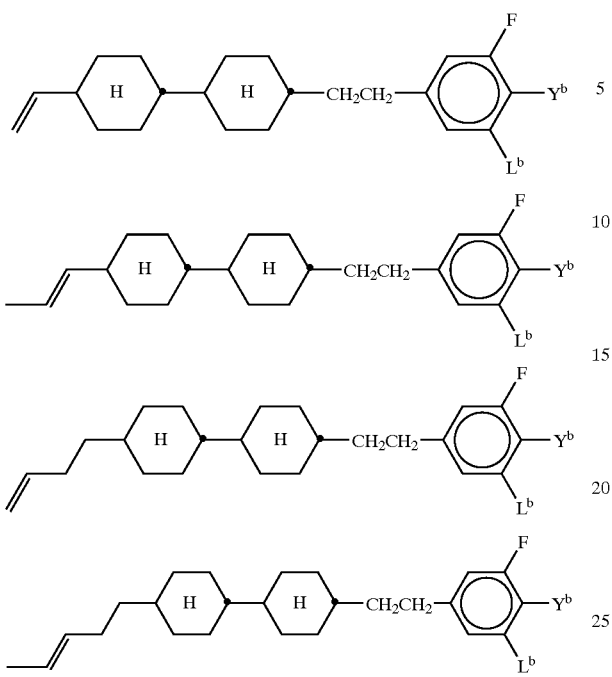

in which $Y^a$, $Y^b$, $L^a$ and $L^b$ are as defined in formulas IA and IB. $L^a$ and/or $L^b$ are preferably fluorine. $Y^a$ and $Y^b$ are preferably each, independently of one another, F or $OCF_3$.

The compounds as such are likewise preferred.

The medium preferably comprises one or more compounds selected from the formulae IIa to IIg, Va, VIa and VIIa (L=H or F):

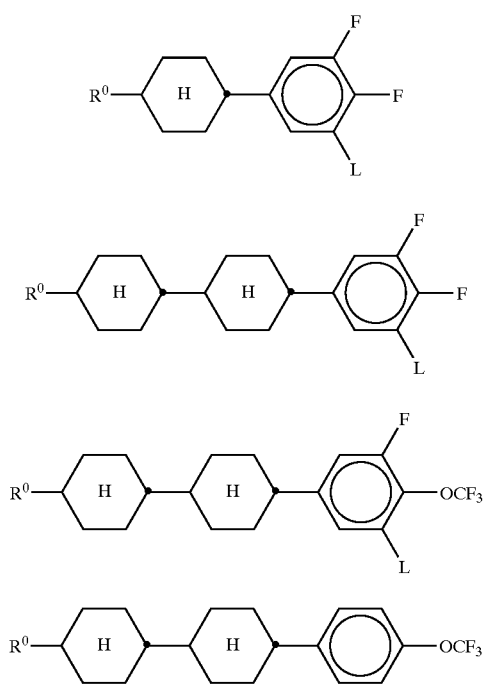

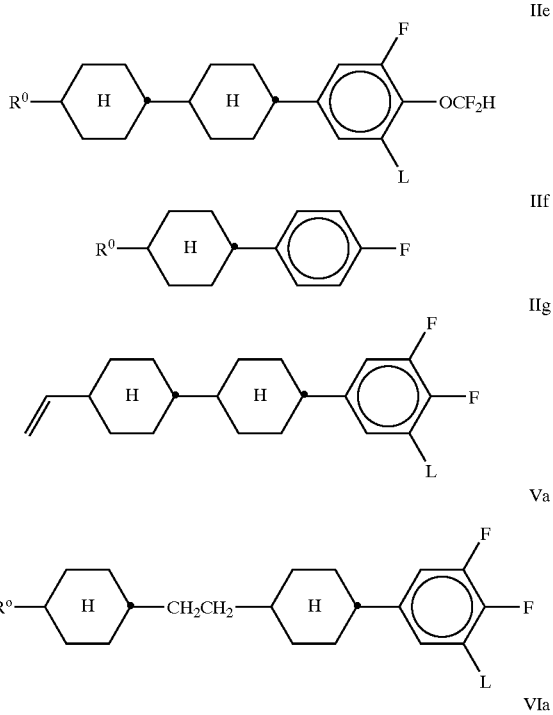

The compounds of the formulae Va and VIa are not identical with the compounds of the formulae IA and IB.

The compounds of the formula IV are preferably

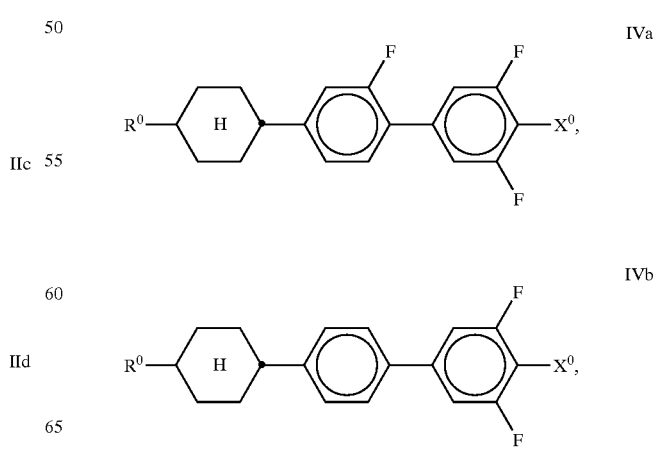

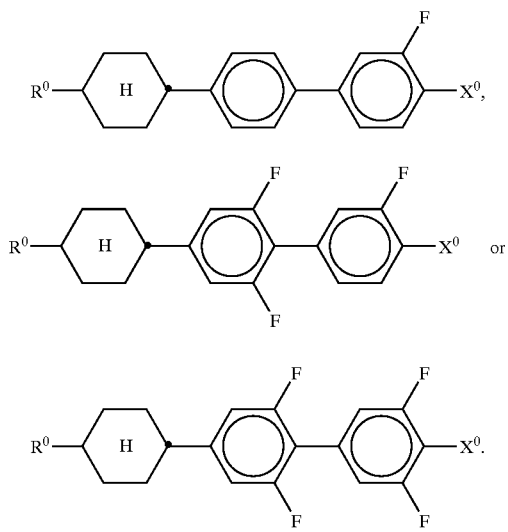

The medium additionally comprises one or more compounds selected from the group consisting of the general formulae IX to XV:

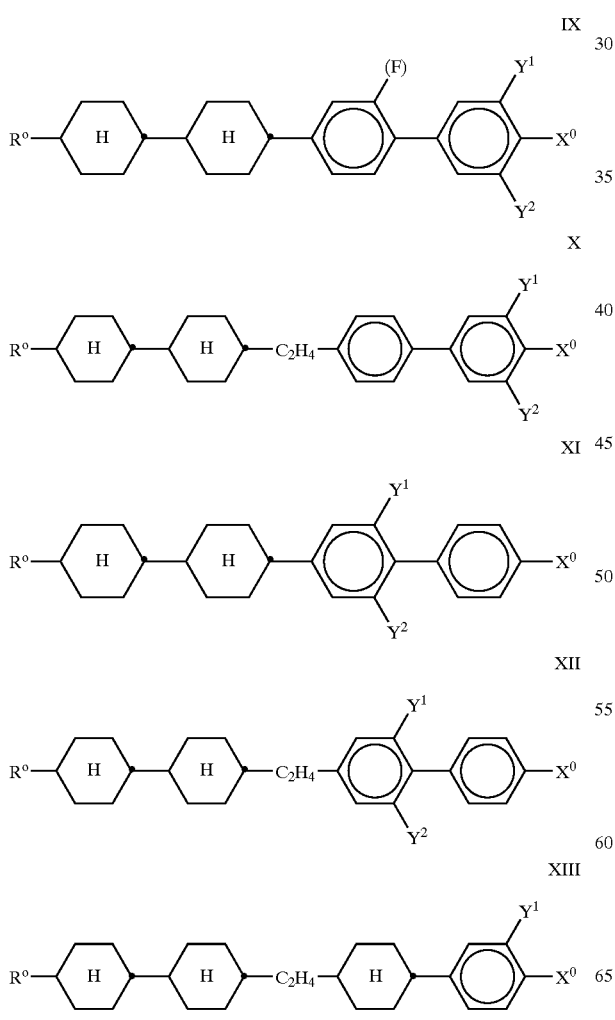

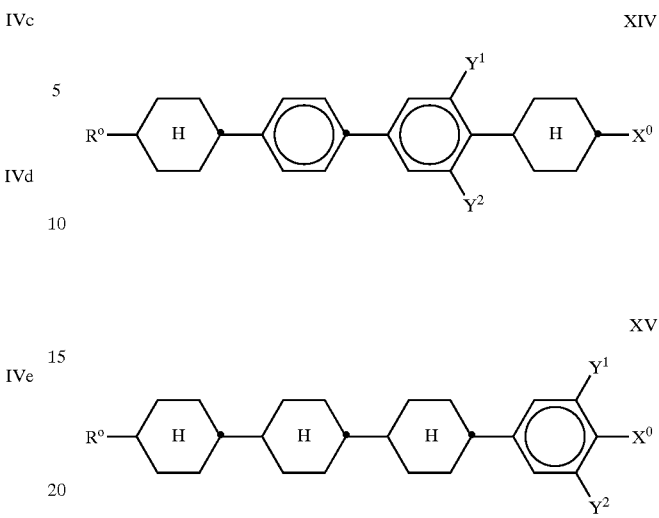

in which $R^0$, $X^0$, $Y^1$ and $Y^2$ are each, independently of one another, as defined in formulas II–VIII and (F) is an optional fluoro substituent. In the compounds of the formulae IX to XV. $X^0$ is preferably F, Cl, $CF_3$, $OCF_3$ or $OCHF_2$. $R^0$ is preferably alkyl, oxaalkyl, alkenyloxy, fluoroalkyl or alkenyl, each having up to 6 carbon atoms.

The medium additionally comprises one or more compounds of the formula DI and/or DII

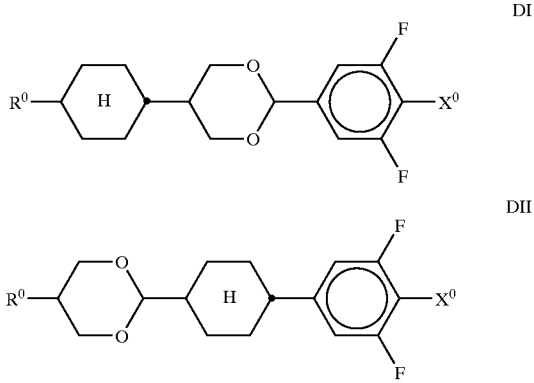

in which $R^0$ and $X^0$ are as defined above;

The medium additionally comprises one or more compounds of the formula

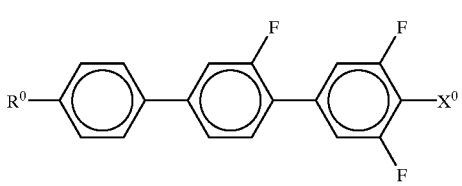

in which $R^0$ and $X^0$ are as defined above;

The medium additionally comprises one or more ester compounds of the formulae E1 to E5:

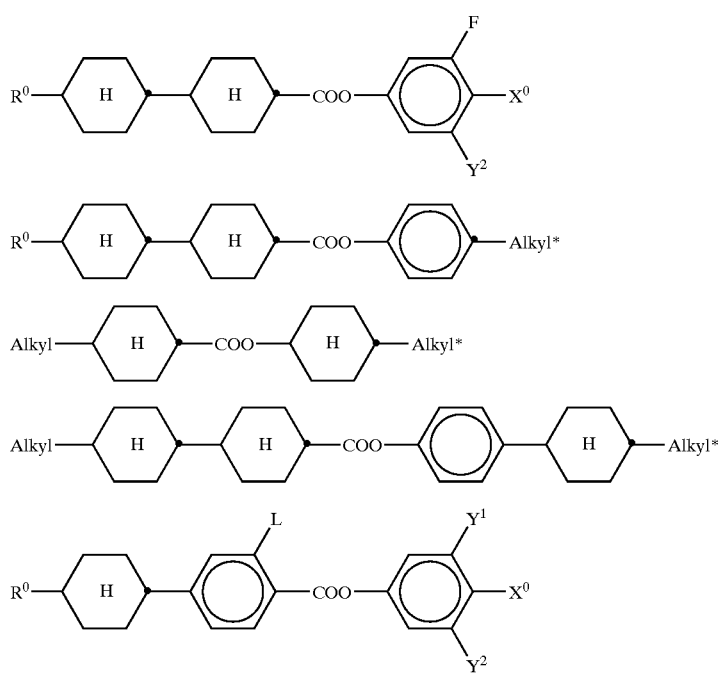

in which $R^0$, $X^0$, $Y^1$ and $Y^2$ are as defined above, and L is H or F.

The medium comprises at least two compounds of the formula E1; in E1, $X^0$ and $Y^2$ are preferably fluorine;

Medium comprises one or more compounds of the formula E1a,

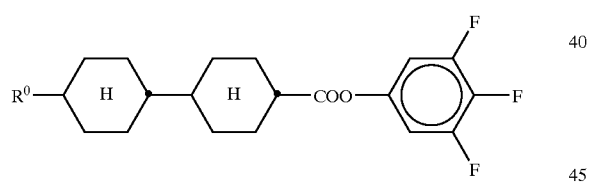

in which $R^0$ is as defined above.

Medium additionally comprises one or more compounds of the formulae Xa to Xf:

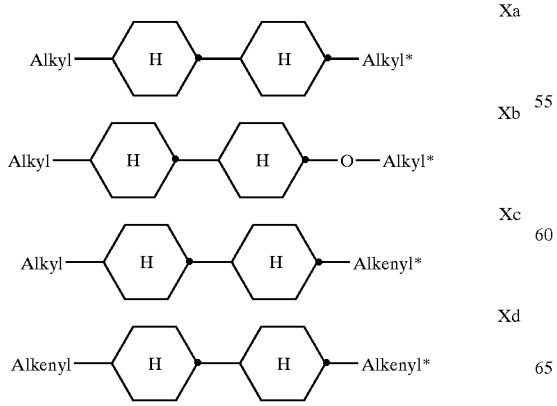

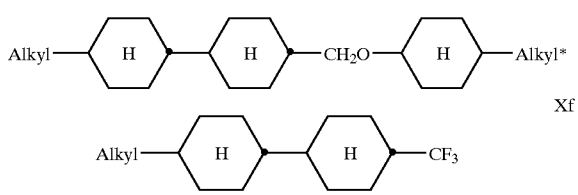

The proportion of compounds of the formulae IA and/or IB and II to VIII together in the mixture as a whole is at least 50% by weight;

The proportion of compounds of the formula IA and/or IB in the mixture as a whole is from 5 to 50% by weight, preferably from 5 to 30% by weight and in particular 5–25% by weight.

The mixture preferably comprises one or two compounds of the formula IA and/or IB;

The proportion of compounds of the formulae II to VIII in the mixture as a whole is from 20 to 80% by weight;

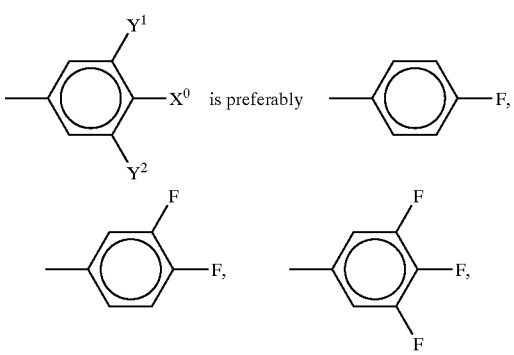

-continued

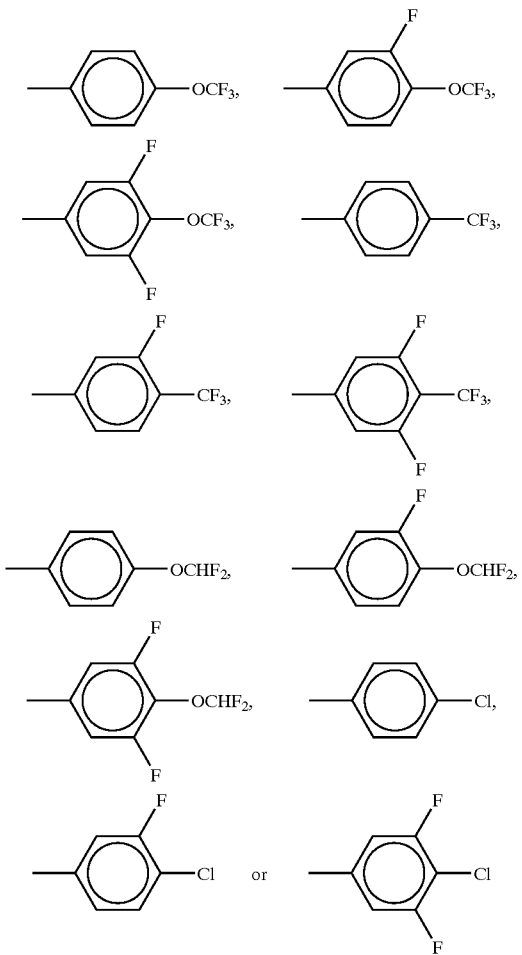

The medium comprises compounds of the formulae II, III, IV, V, VI, VII or VIII;

$R^0$ is straight-chain alkyl or alkenyl having from 2 to 7 carbon atoms;

The medium consists essentially of compounds of the formulae IA and/or IB and II to VIII;

The medium comprises further compounds, preferably selected from the following group consisting of the general formulae XVI to XIX:

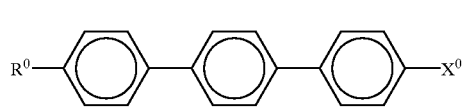

XVI

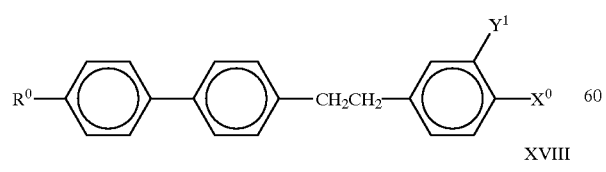

XVII

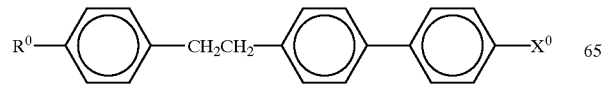

XVIII

-continued

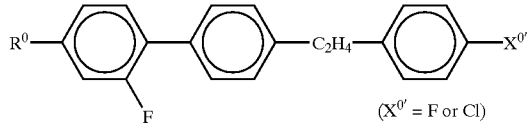

XIX ($X^{0'}$ = F or Cl)

in which $R^0$ and $X^0$ are as defined above, and the 1,4-phenylene rings may be substituted by CN, chlorine or fluorine. The 1,4-phenylene rings are preferably monosubstituted or polysubstituted by fluorine atoms.

The IA and IB: (II+III+IV+V+VI+VII+VIII) weight ratio is preferably from 1:10 to 10:1.

The medium consists essentially of compounds selected from the group consisting of the general formulae IA, IB and II to XV.

The proportion of compounds of the formulae Xa to Xd in the mixture as a whole is 3–45% by weight, especially 5–40% by weight, in particular 5–30% by weight.

The proportion of the compounds of the formula E1 in the mixture as a whole is 10–60% by weight, especially 10–45% by weight, in particular 15–40% by weight.

The proportion of the compounds of the formulae E2 and/or E3 in the mixture as a whole is 1–30% by weight, especially 3–20% by weight and in particular 3–15% by weight.

The proportion of the compounds of the formula E4 is preferably ≦20% by weight, in particular ≦10% by weight.

The medium additionally comprises fluorine-containing fused ring compounds selected from groups A1 to A4:

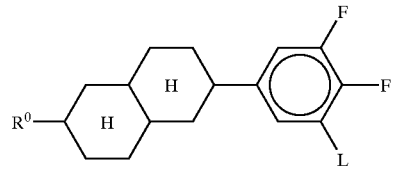

A1

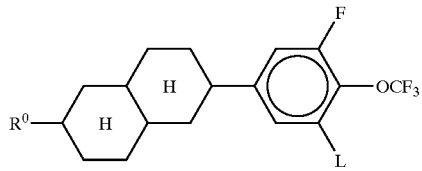

A2

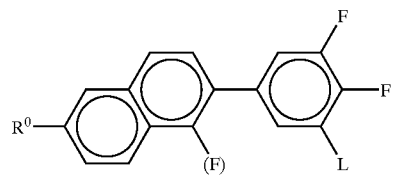

A3

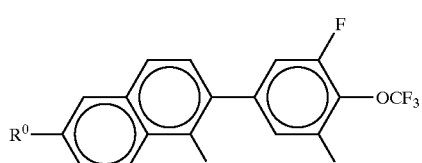

A4 in which $R^0$ is as defined above, L is H or F and (F) represents an optional fluoro substituent. $R^0$ in the compounds of the formulae A1–A4 is preferably a straight-chain alkyl radical.

It has been found that even a relatively small proportion of compounds of the formula IA and/or IB mixed with conventional liquid-crystal materials, but in particular with one or more compounds of the formulae II, III, IV, V, VI, VII and/or VIII, results in a lowering of the threshold voltage and in low birefringence values, with broad nematic phases with low smectic-nematic transition temperatures being observed at the same time, drastically improving the shelf life. Preference is given, in particular, to mixtures which, besides one or more compounds of the formula IA and/or IB, comprise one or more compounds of the formula IV, in particular compounds of the formula IVa in which $X^0$ is F or $OCF_3$.

The compounds of the formulae IA, IB and II to VIII are colorless, stable and readily miscible with one another and with other liquid-crystalline materials.

The term "alkyl" or "alkyl*" covers straight-chain and branched alkyl groups having 1–7 carbon atoms, in particular the straight-chain groups methyl, ethyl, propyl, butyl, pentyl, hexyl and heptyl. Groups having 2–5 carbon 5 atoms are generally preferred.

The term "alkenyl" or "alkenyl*" covers straight-chain and branched alkenyl groups having 2–7 carbon atoms, in particular the straight-chain groups. Particular alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. Preferably, n=1 and m is from 1 to 6.

Through a suitable choice of the meanings of $R^0$ and $X^0$, the response times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio of the elastic constants $k_{33}$ (bend) and $k_{11}$ (splay) compared with alkyl or alkoxy radicals. 4-alkenyl radicals, 3-alkenyl radicals and the like generally give lower threshold voltages and smaller values of $k_{33}/k_{11}$ compared with alkyl and alkoxy radicals.

The optimum mixing ratio of the compounds of the formulae IA/IB and II+III+IV+V+VI+VII+VIII depends substantially on the desired properties, on the choice of the components of the formulae IA, IB, II, III, IV, V, VI, VII and/or VIII, and on the choice of any other components that may be present. Suitable mixing ratios within the range given above can easily be determined from case to case.

The total amount of compounds of the formulae IA, IB and II to XV in the mixtures according to the invention is not crucial. The mixtures can therefore comprise one or more further components for the purposes of optimization of various properties. However, the observed effect on the response times and the threshold voltage is generally greater, the higher the total concentration of compounds of the formulae IA, IB and II to XV.

In a particularly preferred embodiment, the media according to the invention comprise compounds of the formulae II to VIII (preferably II, III and/or IV, in particular IVa) in which $X^0$ is F, $OCF_3$, $OCHF_2$, F, $OCH=CF_2$, $OCF=CF_2$ or $OCF_2$—$CF_2H$. A favorable synergistic effect with the compounds of the formula IA and/or IB results in particularly advantageous properties. In particular, mixtures comprising compounds of the formula IA and/or IB and of the formula IVa are distinguished by their low threshold voltages.

The construction of the STN or MLC display according to the invention from polarizers, electrode base plates and surface-treated electrodes corresponds to the conventional construction for displays of this type. The term conventional construction is broadly drawn here and also covers all derivatives and modifications of the MLC display, in particular including matrix display elements based on poly-Si TFT or MIM and very particularly reflective displays.

A significant difference between the displays according to the invention and the conventional displays based on the twisted nematic cell consists, however, in the choice of the liquid-crystal parameters of the liquid-crystal layer.

The liquid-crystal mixtures which can be used in accordance with the invention are prepared in a manner conventional per se. In general, the desired amount of the components used in the lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multi-bottle" systems.

The dielectrics may also comprise further additives known to the person skilled in the art and described in the literature. For example, 0–15%, preferably 0–10%, of pleochroic dyes and/or chiral dopants can be added. The individual compounds added are employed in concentrations of from 0.01 to 6%, preferably from 0.1 to 3%. However, the concentration figures for the other constituents of the liquid-crystal mixtures, i.e. of the liquid-crystalline or mesogenic compounds, are indicated without taking into account the concentration of these additives.

C denotes a crystalline phase, S a smectic phase, $S_C$ a smectic C phase, N a nematic phase and I the isotropic phase.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is indicated. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| V-T | $CH_2$=CH | CF$_3$ | H | H |
| V2-T | $CH_2$=CH—$C_2H_4$ | CF$_3$ | H | H |
| 1V-OT | $CH_3$—CH=CH | OCF$_3$ | H | H |
| rEsN | $C_rH_{2r+1}$—O—$C_sH_{2s}$— | CN | H | H |
| nAm | $C_nH_{2n+1}$ | COOC$_m$H$_{2m+1}$ | H | H |
| nOCCF$_2$.F.F | $C_nH_{2n+1}$ | OCH$_2$CF$_2$H | F | F |

Preferred mixture components are given in Tables A and B.

TABLE A

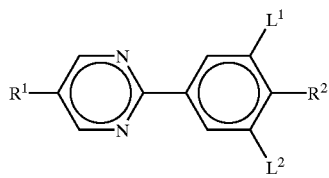

PYP

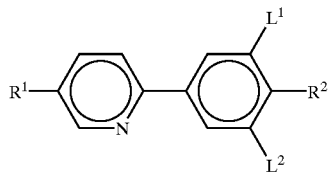

PYRP

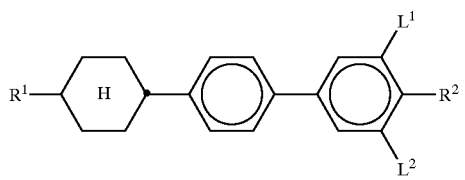

BCH

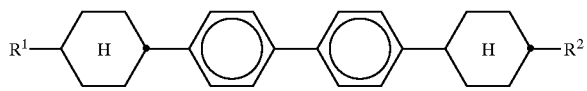

CBC

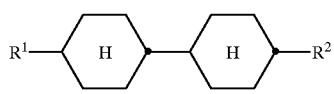

CCH

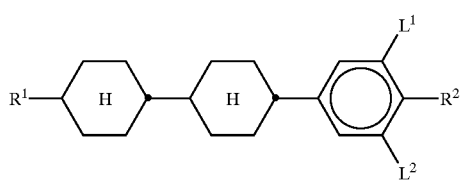

TABLE A-continued
CCP
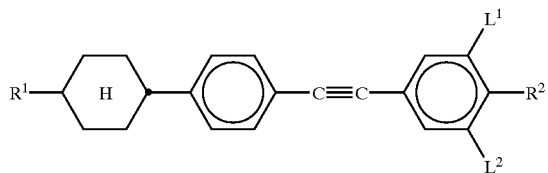
CPTP
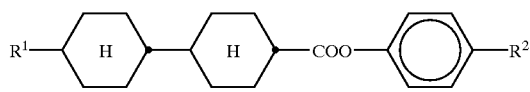
CP
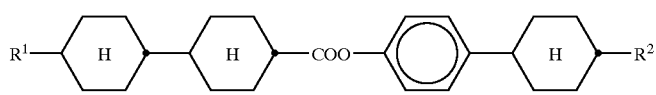
CCPC
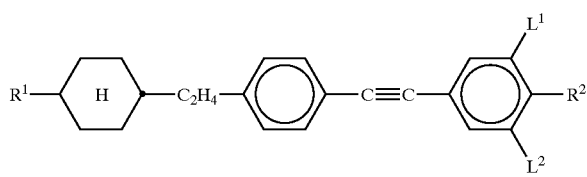
CEPTP
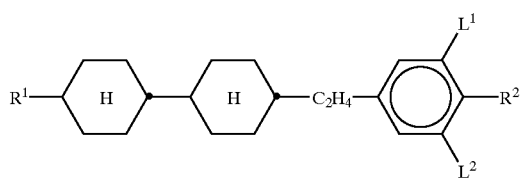
ECCP
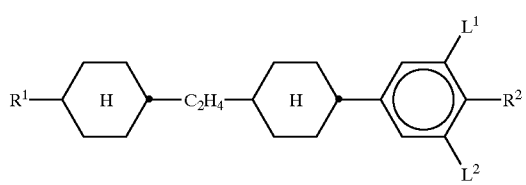
CECP
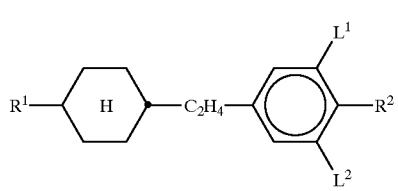
EPCH TABLE A-continued
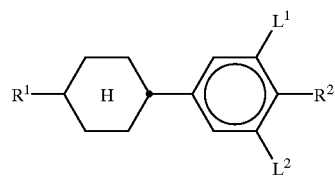
PCH
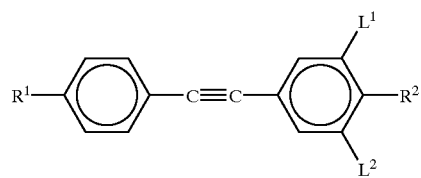
PTP
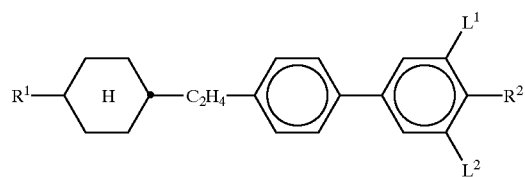
BECH
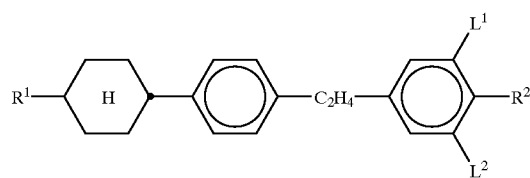
EBCH
CPC
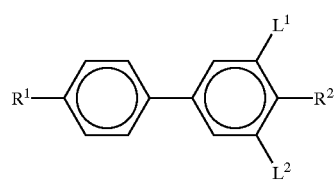
B
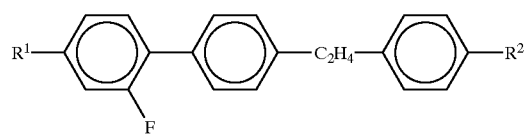
FET-nF
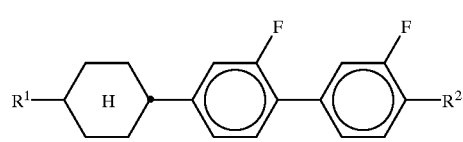

TABLE A-continued
CGG
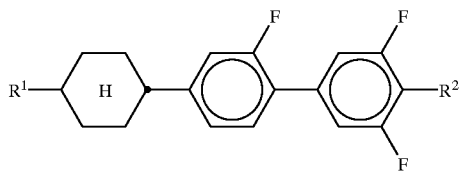
CGU
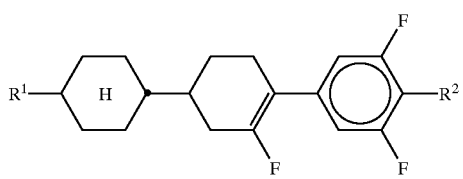
CFU
TABLE B
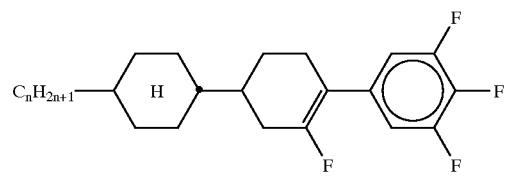
BCH-n.Fm
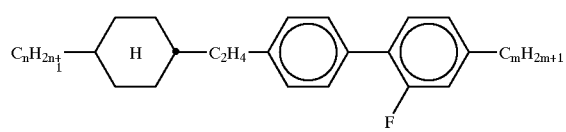
CFU-n-F
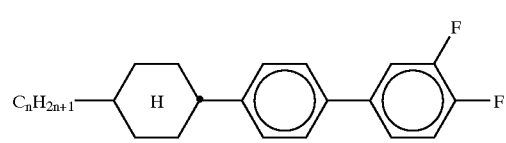
Inm
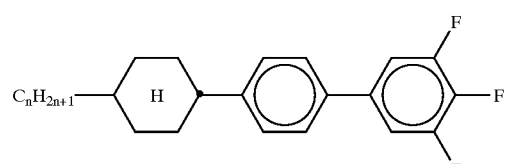
BCH-nF.F
BCH-nF.F.F
TABLE B-continued
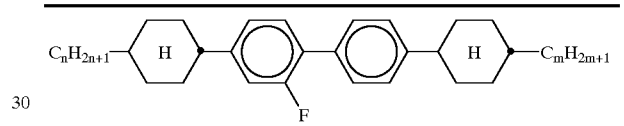
CBC-nmF
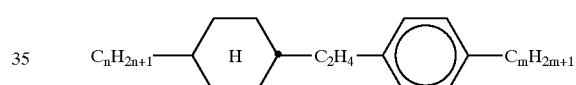
ECCP-nm
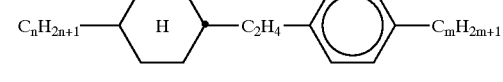
CCH-n1EM
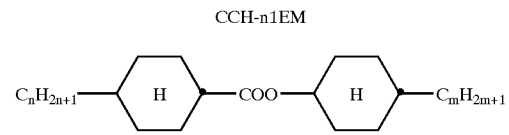
OS-nm
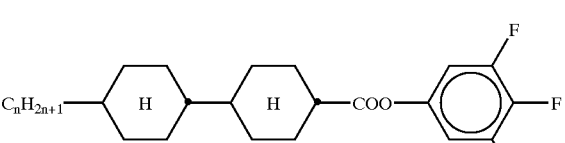
CCZU-n-F
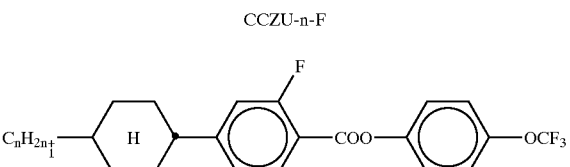
CGZP-n-OT TABLE B-continued
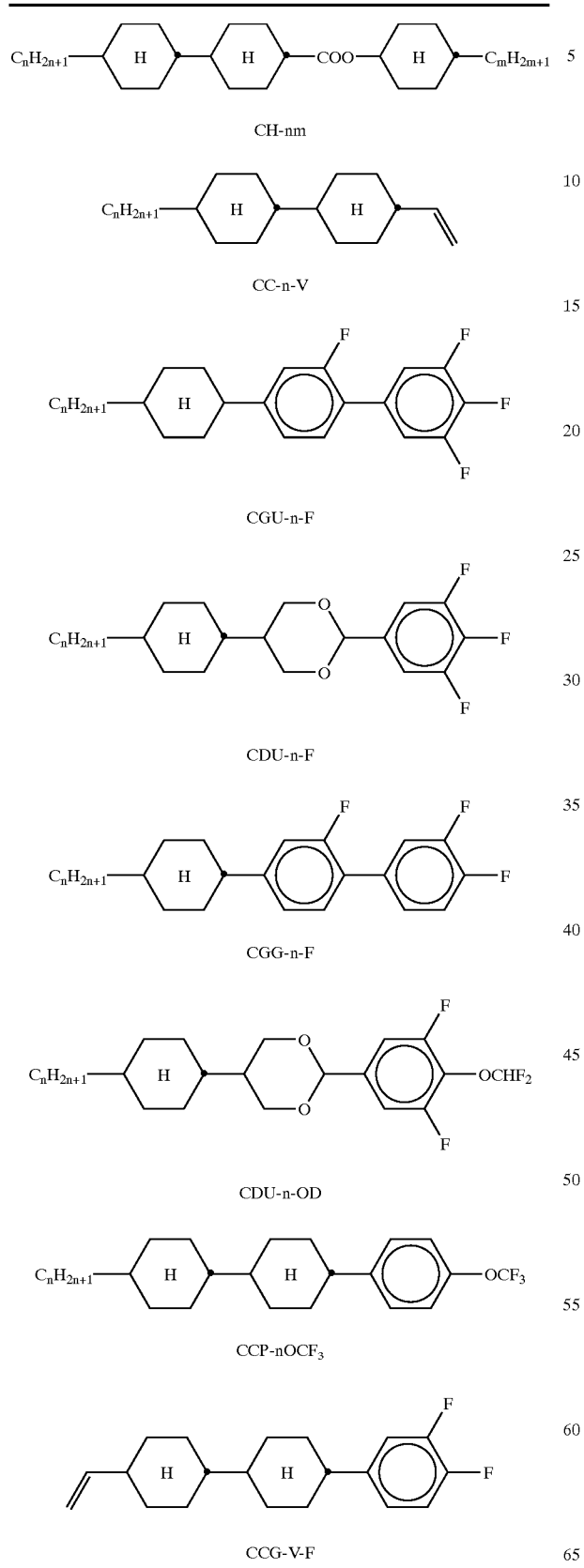
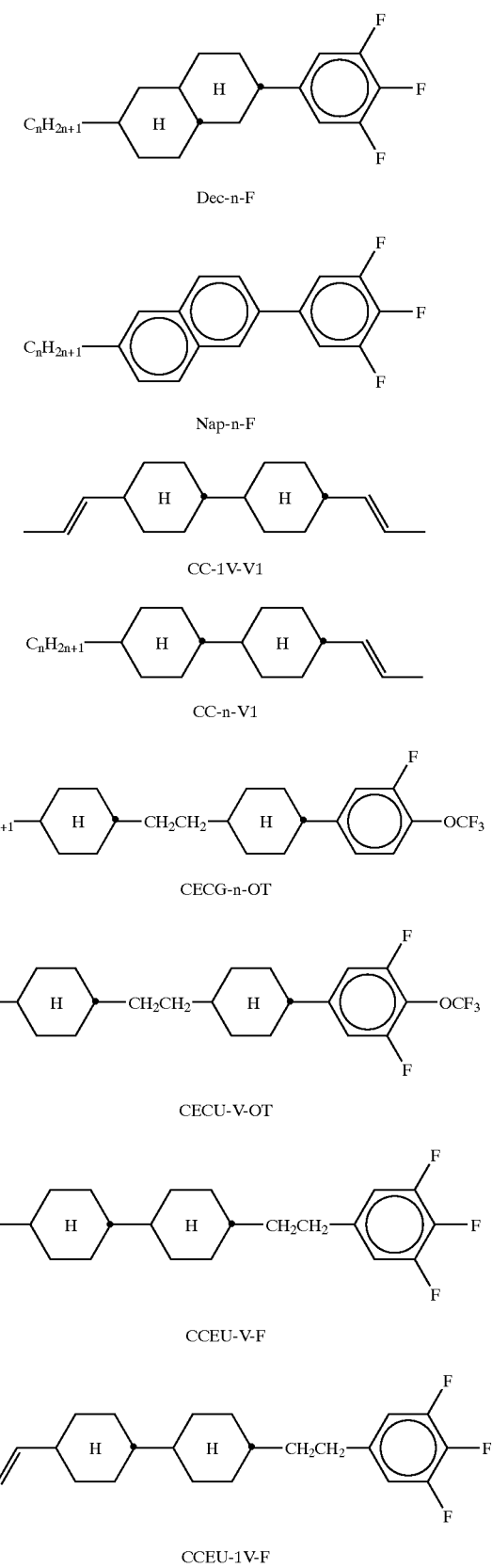

TABLE B-continued
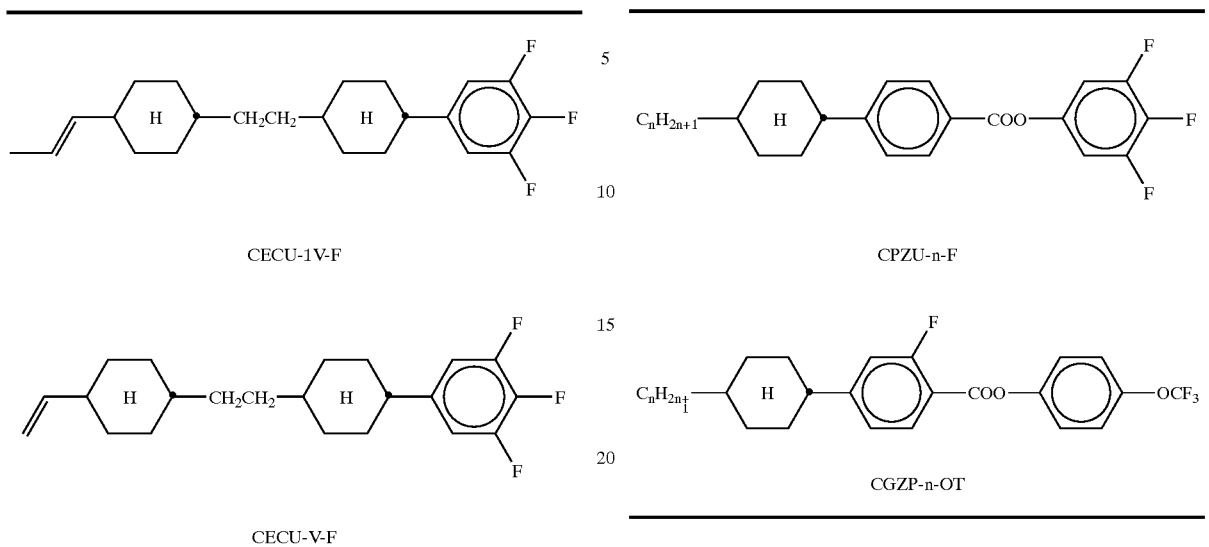
CECU-1V-F
CECU-V-F
CPZU-n-F
CGZP-n-OT
TABLE C
Table C indicates possible dopants which are generally added to the mixtures according to the invention.
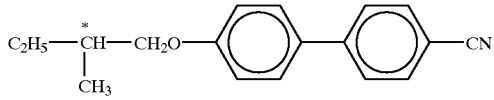
C 15
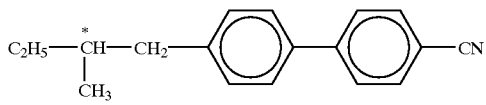
CB 15
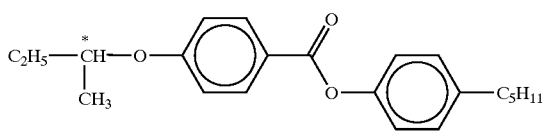
CM 21
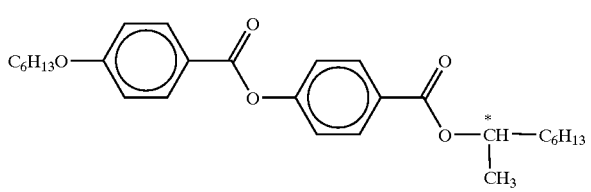
R/S 811
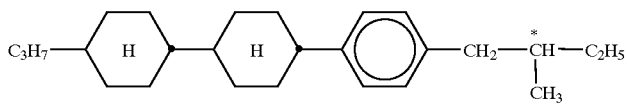
CM 44

TABLE C-continued
Table C indicates possible dopants which are generally added to the mixtures according to the invention.
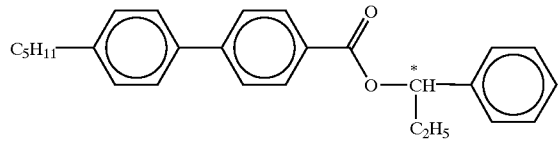
CM 45
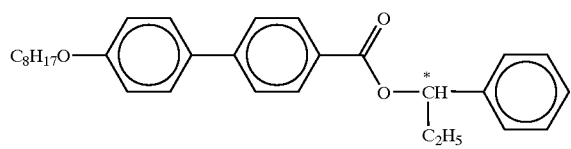
CM 47
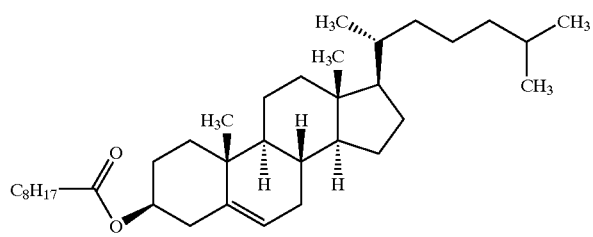
CN
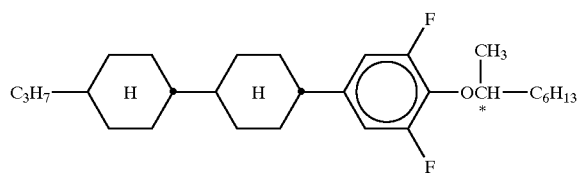
R/S 2011
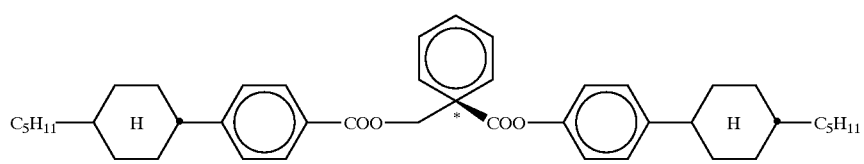
R/S-1011
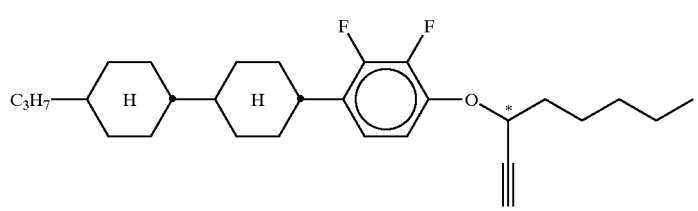

TABLE C-continued

Table C indicates possible dopants which are generally added to the mixtures according to the invention.

R/S-3011

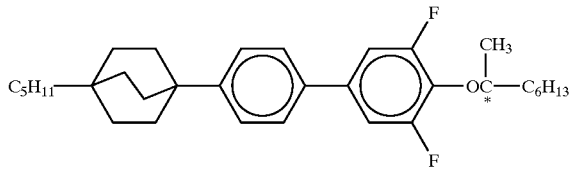

R/S-4011

The entire disclosure of all applications, patents and publications cited above and below, and of corresponding German application No. 100 50 405.1, filed Oct. 12, 2000 is hereby incorporated by reference.

EXAMPLES

The following examples are intended to explain the invention without restricting it. Above and below, percentages are per cent by weight. All temperatures are given in degrees Celsius. m.p. denotes melting point, cl.p.=clearing point. Furthermore, C=crystalline state, N=nematic phase, S=smectic phase and I=isotropic phase. The data between these symbols represent the transition temperatures. The optical anisotropy (589 nm, 20° C.), and the flow viscosity $v_{20}$ (mm$^2$/sec) and the rotational viscosity $\gamma_1$ (mPa·s) were each determined at 20° C.

$V_{10}$ denotes the voltage for 10% transmission (viewing angle perpendicular to the plate surface). $t_{on}$ denotes the switch-on time and $t_{off}$ the switch-off time at an operating voltage corresponding to twice the value of $V_{10}$. An denotes the optical anisotropy and no the refractive index. Δ∈ denotes the dielectric anisotropy (Δ∈=∈$_\parallel$−∈$_\perp$, where ∈$_\parallel$ denotes the dielectric constant parallel to the longitudinal molecular axes and ∈$_\perp$ denotes the dielectric constant perpendicular thereto). The electro-optical data were measured in a TN cell at the 1st minimum (i.e. at a d·Δn value of 0.5) at 20° C., unless expressly stated otherwise. The optical data were measured at 20° C., unless expressly stated otherwise.
Mixture examples

| Example A | | | |
|---|---|---|---|
| CCP-2F.F.F | 6.0% | Clearing point [° C.]: | 67.5° C. |
| CCP-30CF$_3$.F | 4.0% | Δn [589 nm. 20° C.]: | +0.0918 |
| CCG-V-F | 1.0% | Δε [1 kHz. 20° C.]: | 10.7 |
| CCP-30CF$_3$ | 6.0% | γ$_2$ [mPa.s. 20° C.]: | 139 |
| CCP-50CF$_3$ | 2.0% | d·Δn [μm. 20° C.]: | 0.5 |
| CGU-2-F | 11.0% | Twist: | 90° |
| CGU-3-F | 11.0% | | |
| BCH-3F.F.F | 4.0% | | |
| CCZU-2-F | 7.0% | | |
| CCZU-3-F | 14.0% | | |
| CCZU-5-F | 7.0% | | |
| CCEU-V-F | 11.0% | | |
| CCEU-1V-F | 6.0% | | |
| Example B | | | |
| CCP-2F.F.F | 6.0% | Clearing point [° C.]: | 66.3° C. |
| CCP-3F.F.F | 4.0% | Δn [589 nm. 20° C.]: | +0.0914 |
| CCP-30CF$_3$.F | 4.0% | Δε [1 kHz. 20° C.]: | 10.8 |
| CCG-V-F | 1.0% | γ$_2$ [mPa.s. 20° C.]: | 144 |
| CCP-30CF$_3$ | 6.0% | d·Δn [μm. 20° C.]: | 0.5 |
| CCP-50CF$_3$ | 2.0% | Twist: | 90° |
| CGU-2-F | 11.0% | | |
| CGU-3-F | 11.0% | | |
| CGU-5-F | 10.0% | | |
| BCH-3F.F.F | 6.0% | | |
| CCZU-2-F | 7.0% | | |
| CCZU-3-F | 14.0% | | |
| CCZU-5-F | 7.0% | | |
| CECU-V-F | 4.0% | | |
| CECU-1V-F | 7.0% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid-crystalline medium based on a mixture of polar compounds of positive dielectric anisotropy, comprising one or more compounds of the formula IA and/or formula IB

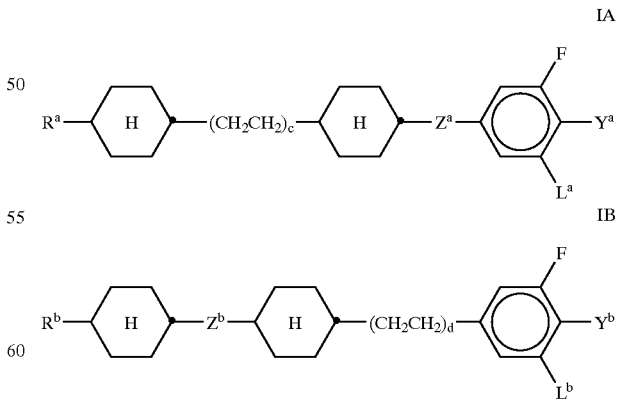

in which
    R$^a$ and R$^b$ are each, independently of one another, an alkenyl radical having up to 15 carbon atoms which is unsubstituted, monosubstituted by CN or CF$_3$ or at least monosubstituted by halogen, where, in addition, one or more CH$_2$ groups in these radicals may each, independently of one another, be replaced by —O—, —S—,

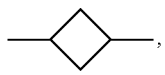

—CO—, —CO—O—, —O—CO— or —O—CO—O— in such a way that O atoms are not linked directly to one another, Y$^a$ and Y$^b$ are each, independently of one another, F, Cl, SF$_5$, NCS, or a halogenated alkyl, alkoxy, alkenyl or alkenyloxy radical having up to 5 carbon atoms, L$^a$ and L$^b$ are each, independently of one another, H or F, Z$^a$ and Z$^b$ are each, independently of one another, —COO—, —CH$_2$O—, —OCH$_2$—, —C$_2$F$_4$—, —CF$_2$O—, —OCF$_2$— or a single bond, and c and d are each, independently of one another, 1 or 2;

wherein said medium further comprises one or more compounds selected from formulae II, III, IV, V, VI, VII and VIII:

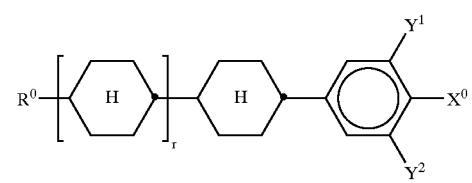 II

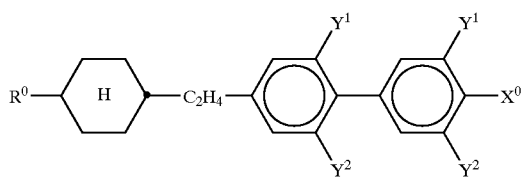 III

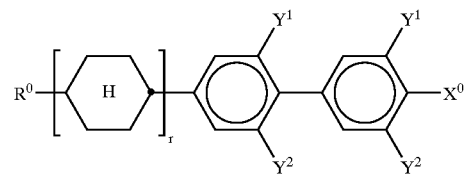 IV

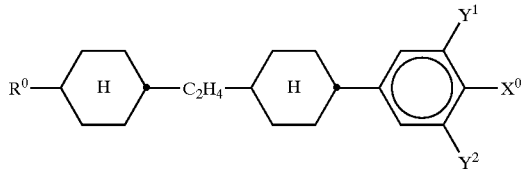 V

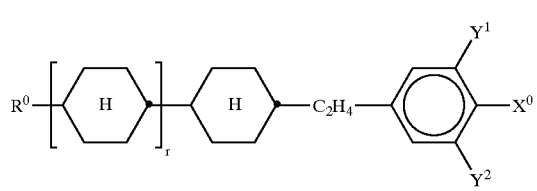 VI

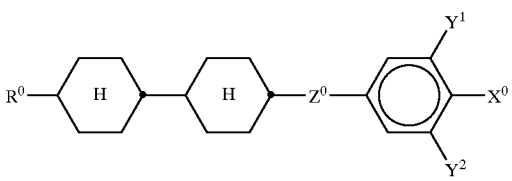 VII

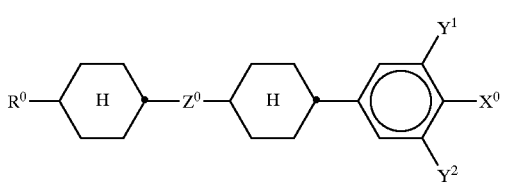 VIII wherein
R$^0$ in each case is, independently, alkyl, oxaalkyl, fluoroalkyl or alkenyl, each having up to 9 carbon atoms, X$^0$ in each case is, independently, F, Cl, halogenated alkyl or alkoxy having 1 to 6 carbon atoms, or halogenated, alkenyl or alkenyloxy having up to 6 carbon atoms, Z$^0$ in each case is, independently, —C$_4$H$_8$—, —C$_2$F$_4$—, —OCH$_2$—, —CH$_2$O—, —CF$_2$O—, —OCF$_2$— or —CF=CF—, Y$^1$ and Y$^2$ are in each case, independently of one another, H or F, and r is 0 or 1.

2. A medium according to claim 1, wherein the proportion of compounds of formulae IA and/or IB and formulae II to VIII together in the mixture as a whole is at least 50% by weight.

3. A medium according to claim 1, wherein the proportion of compounds of formula IA and/or IB in the mixture as a whole is 5–50% by weight.

4. A medium according to claim 2, wherein the proportion of compounds of formula 1A and/or 1B in the mixture as a whole is 5–50% by weight.

5. A medium according to claim 1, wherein the proportion of compounds of formulae II to VIII in the mixture as a whole is 20–80% by weight.

6. A medium according to claim 2, wherein the proportion of compounds of formulae II to VIII in the mixture as a whole is 20–80% by weight.

7. A medium according to claim 4, wherein the proportion of compounds of formulae II to VIII in the mixture as a whole is 20–80% by weight.

8. A medium according to claim 1, further comprising one or more compounds of formula E1

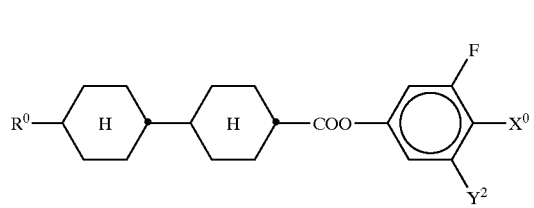 E1 wherein
R$^0$ is alkyl, oxaalkyl, fluoroalkyl or alkenyl, each having up to 9 carbon atoms, X$^0$ is F, Cl, halogenated alkyl or alkoxy having 1 to 6 carbon atoms, or halogenated, alkenyl or alkenyloxy having up to 6 carbon atoms, and $Y^2$ is H or F.

9. A medium according to claim 8, wherein $X^0$ is F or $OCF_3$, and $Y^2$ is H or F.

10. A medium according to claim 1, further comprising one or more compounds of formula IVa

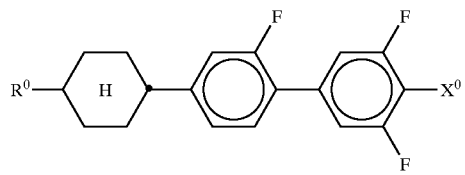

wherein $R^0$ is alkyl, oxaalkyl, fluoroalkyl or alkenyl, each having up to 9 carbon atoms, and $X^0$ is F, Cl, halogenated alkyl or alkoxy having 1 to 6 carbon atoms, or halogenated, alkenyl or alkenyloxy having up to 6 carbon atoms.

11. A medium according to one of claim 1, wherein said compounds of formulae IA and IB are selected from formulas IAa–IAh and IBa–IBh:

IAa

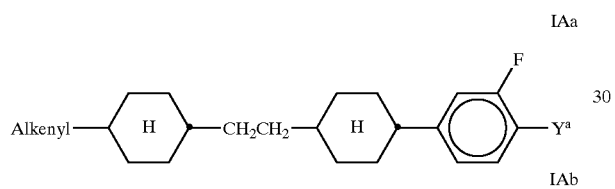

IAb

IAc

IAd

IAe

IAf

IAg

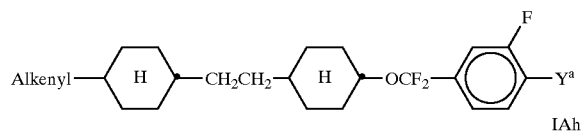

IAh

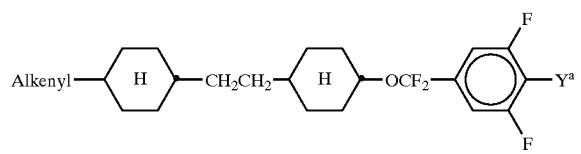

IBa

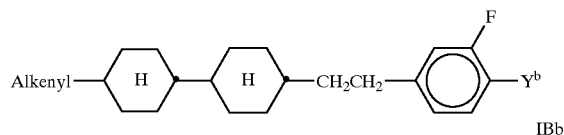

IBb

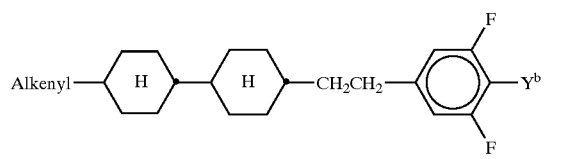

IBc

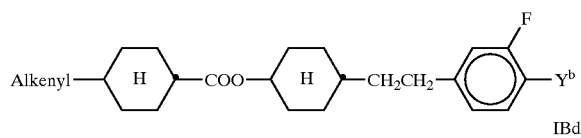

IBd

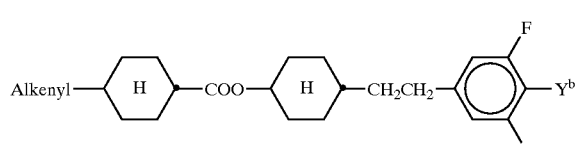

IBe

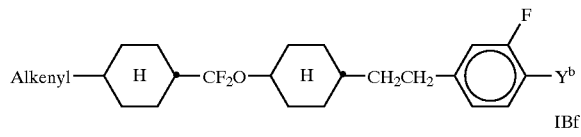

IBf

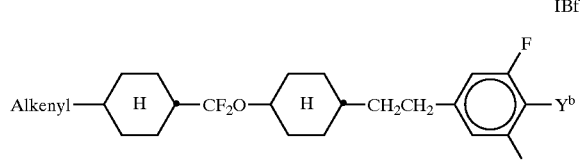

IBg

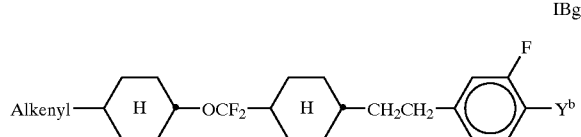

IBh

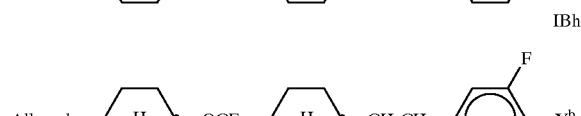

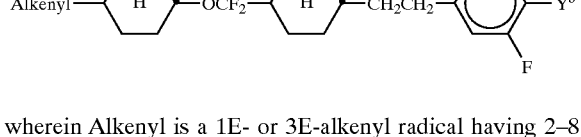

wherein Alkenyl is a 1E- or 3E-alkenyl radical having 2–8 carbon atoms.

12. In an electro-optical liquid-crystal display containing a liquid-crystalline medium, the improvement wherein said medium is in accordance with claim 1.

13. In a method of generating an electro-optical effect using an electro-optical liquid-crystal display, the improvement wherein said display is in accordance with claim 12.

14. A compound of formula IA or formula IB

, in which

R$^a$ and R$^b$ are each, independently of one another, an alkenyl radical having up to 15 carbon atoms which is unsubstituted, monosubstituted by CN or CF$_3$ or at least monosubstituted by halogen, where, in addition, one or more CH$_2$ groups in these radicals may each, independently of one another, be replaced by —O—, —S—,

IA

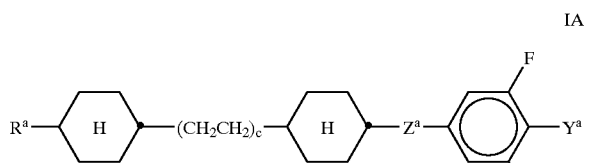

IB

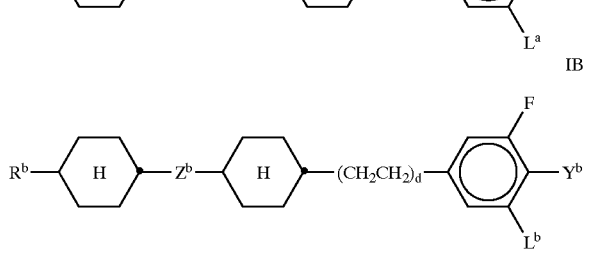

—O—, —CO—O—, —O—CO— or —O—CO—O— in such a way that O atoms are not linked directly to one another, Y$^a$ and Y$^b$ are each, independently of one another, F, Cl, SF$_5$, NCS, or a halogenated alkyl, alkoxy, alkenyl or alkenyloxy radical having up to 5 carbon atoms, L$^a$ and L$^b$ are each, independently of one another, H or F, Z$^a$ and Z$^b$ are each, independently of one another, —COO—, —CH$_2$CH$_2$—, —CH$_2$O—, —OCH$_2$—, —C$_2$F$_4$—, —CF$_2$O—, —OCF$_2$— or a single bond, and c and d are each, independently of one another, 1 or 2.

15. A compound according to claim 14, wherein at least one of Y$^a$ and Y$^b$ are each independently F, OCHFCF$_3$, OCF$_3$, OCHF$_2$, OC$_2$F$_5$, OC$_3$F$_7$, OCH=CF$_2$ or CF$_2$OCF$_3$.

16. A compound according to claim 14, wherein at least one of Y$^a$ and Y$^b$ is F or OCF$_3$, L$^a$ and L$^b$ are each F, Z$^a$ and Z$^b$ are each independently a single bond, —CF$_2$O— or —COO—, and c and d are each 1.

17. A liquid crystal medium according to claim 1, wherein said medium has a nematic phase down to −30° C. and a clearing point above 65° C.

18. A liquid crystal medium according to claim 1, wherein said medium has a birefringence value of ≧0.095.

19. A liquid crystal medium according to claim 1, wherein said medium has a TN threshold below 1.7 V.

20. A liquid crystal medium according to claim 11, wherein Alkenyl is vinyl, CH$_3$CH=CH, CH$_2$=CHC$_2$H$_4$ or CH$_3$CH=CHC$_2$H$_4$.

21. A medium according to claim 1, further comprising one or more compounds selected from formulae IX to XV:

IX

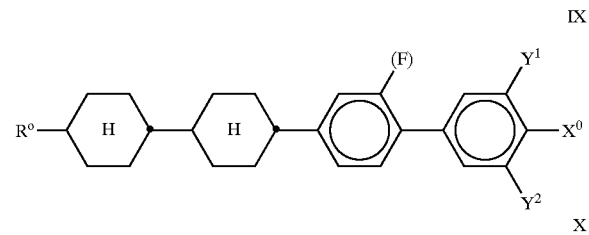

X

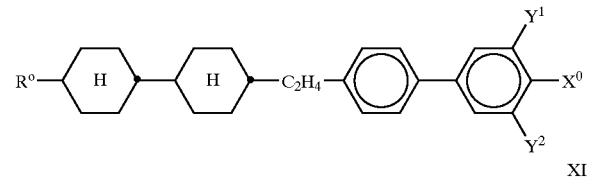

XI

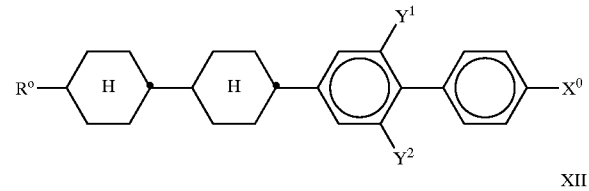

XII

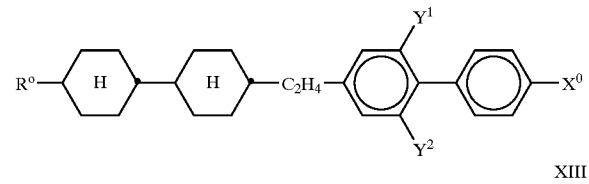

XIII

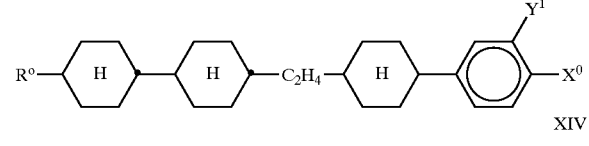

XIV

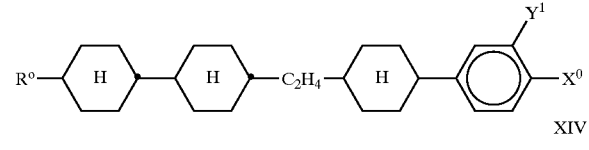

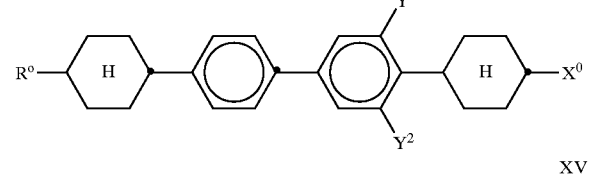

XV

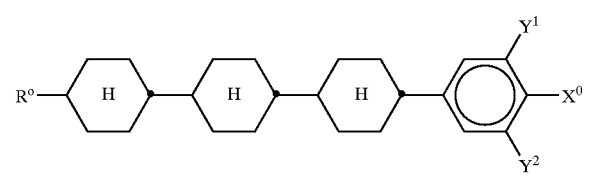

wherein

R$^0$ in each case is, independently, alkyl, oxaalkyl, fluoroalkyl or alkenyl, each having up to 9 carbon atoms, X$^0$ in each case is, independently, F, Cl, halogenated alkyl or alkoxy having 1 to 6 carbon atoms, or halogenated, alkenyl or alkenyloxy having up to 6 carbon atoms, Y$^1$ and Y$^2$ are in each case, independently of one another, H or F, and (F) is an optional fluoro substituent.

22. A liquid crystal medium according to claim 21, wherein in the compounds of formulae IX to XV, X$^0$ is F, Cl, CF$_3$, OCF$_3$ or OCHF$_2$, and R$^0$ alkyl, oxaalkyl, alkenyloxy, fluoroalkyl or alkenyl, each having up to 6 carbon atoms.

23. A medium according to claim 1, further comprising one or more compounds selected from formulae DI and/or DII

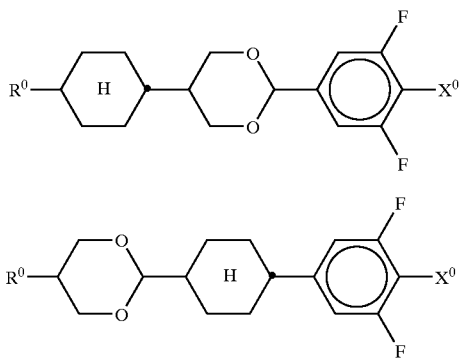

DI

DII wherein

R$^0$ in each case is, independently, alkyl, oxaalkyl, fluoroalkyl or alkenyl, each having up to 9 carbon atoms, and X$^0$ in each case is, independently, F, Cl, halogenated alkyl or alkoxy having 1 to 6 carbon atoms, or halogenated, alkenyl or alkenyloxy having up to 6 carbon atoms.

24. A medium according to claim 1, further comprising one or more compounds selected from the formula

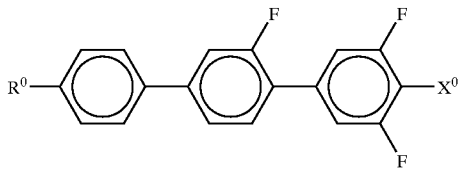

wherein

R$^0$ in each case is, independently, alkyl, oxaalkyl, fluoroalkyl or alkenyl, each having up to 9 carbon atoms, and X$^0$ in each case is, independently, F, Cl, halogenated alkyl or alkoxy having 1 to 6 carbon atoms, or halogenated, alkenyl or alkenyloxy having up to 6 carbon atoms.

25. A medium according to claim 1, further comprising one or more compounds selected from formula E1a,

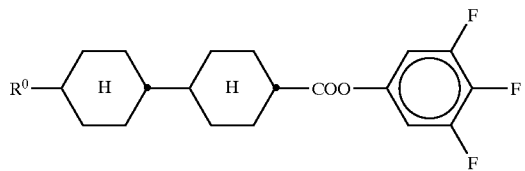

E1a in which R$^0$ is alkyl, oxaalkyl, fluoroalkyl or alkenyl, each having up to 9 carbon atoms.

26. A medium according to claim 1, wherein the proportion of compounds of formula IA and/or IB in the mixture as a whole is 11–25% by weight.

27. A medium according to claim 1, wherein the proportion of compounds of formula IA and/or IB in the mixture as a whole is 17–25% by weight.

28. A medium according to claim 1, further comprising one or more compounds selected from the formula formulae XVI to XIX:

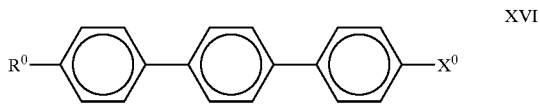

XVI

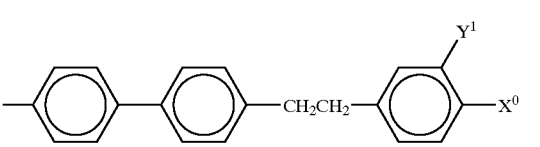

XVII

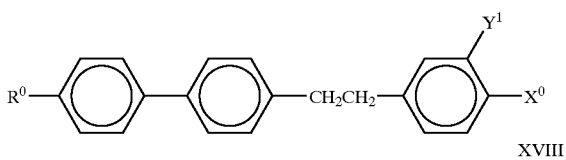

XVIII

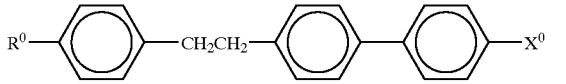

XIX wherein

R$^0$ in each case is, independently, alkyl, oxaalkyl, fluoroalkyl or alkenyl, each having up to 9 carbon atoms, X$^0$ in each case is, independently, F, Cl, halogenated alkyl or alkoxy having 1 to 6 carbon atoms, or halogenated, alkenyl or alkenyloxy having up to 6 carbon atoms, X$^0$ is F or Cl, Y$^1$ is H or F, and the 1,4-phenylene rings are optionally substituted by CN, chlorine or fluorine.

29. A medium according to claim 1, wherein the weigh ratio of compounds formula IA and IB to compounds of formula II+III+IV+V+VI+VII+VIII is 1:10 to 10:1.

* * * * *

UNITED STATES PATENT AND TRADEMARK OFFICE
CERTIFICATE OF CORRECTION

PATENT NO. : 6,696,111 B2  
APPLICATION NO. : 09/973720  
DATED : February 24, 2004  
INVENTOR(S) : Michael Heckmeier It is certified that error appears in the above-identified patent and that said Letters Patent is hereby corrected as shown below:

Column 41, line 10 reads "  ' " should read
--

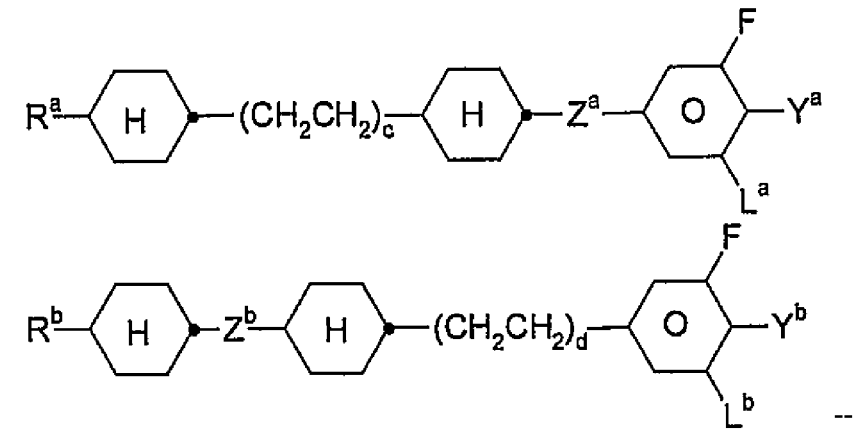

--

UNITED STATES PATENT AND TRADEMARK OFFICE
CERTIFICATE OF CORRECTION

PATENT NO. : 6,696,111 B2
APPLICATION NO. : 09/973720
DATED : February 24, 2004
INVENTOR(S) : Michael Heckmeier It is certified that error appears in the above-identified patent and that said Letters Patent is hereby corrected as shown below:

Column 41, line 25 reads

"
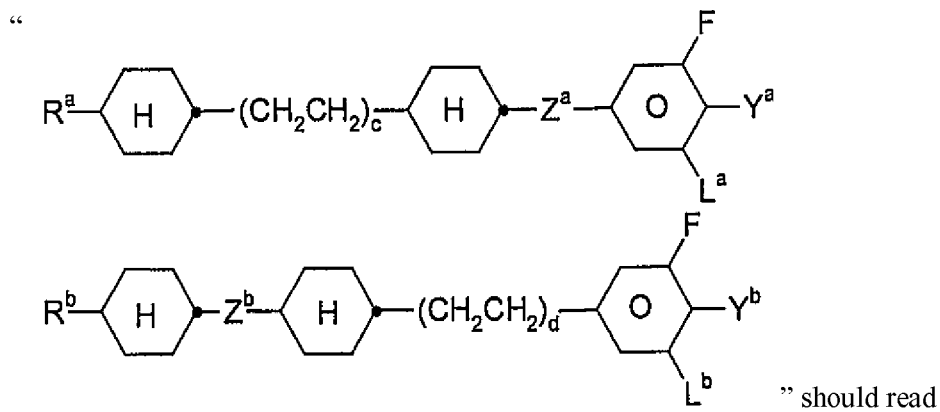
" should read

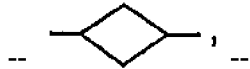

Signed and Sealed this

Sixth Day of February, 2007

JON W. DUDAS
*Director of the United States Patent and Trademark Office*